(12) United States Patent
Biondo et al.

(10) Patent No.: US 9,975,552 B2
(45) Date of Patent: May 22, 2018

(54) METHOD AND APPARATUS FOR DETECTING PROJECTED IMPAIRMENT

(71) Applicant: GM GLOBAL TECHNOLOGY OPERATIONS LLC, Detroit, MI (US)

(72) Inventors: William A. Biondo, Beverly Hills, MI (US); David T. Proefke, Troy, MI (US); Fred W. Huntzicker, Ann Arbor, MI (US); Stephane Vitet, Frankfurt am Main (DE)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 68 days.

(21) Appl. No.: 15/229,625

(22) Filed: Aug. 5, 2016

(65) Prior Publication Data

US 2018/0037228 A1 Feb. 8, 2018

(51) Int. Cl.
| | |
|---|---|
| *B60W 30/18* | (2012.01) |
| *B60W 10/06* | (2006.01) |
| *B60W 10/10* | (2012.01) |
| *B60W 10/18* | (2012.01) |
| *B60K 28/06* | (2006.01) |
| *B60K 35/00* | (2006.01) |
| *A61B 5/18* | (2006.01) |
| *A61B 5/00* | (2006.01) |

(52) U.S. Cl.
CPC .............. *B60W 30/18* (2013.01); *A61B 5/18* (2013.01); *A61B 5/4845* (2013.01); *B60K 28/063* (2013.01); *B60K 35/00* (2013.01); *B60W 10/06* (2013.01); *B60W 10/10* (2013.01); *B60W 10/18* (2013.01); *B60K 2350/1096* (2013.01); *B60W 2540/24* (2013.01)

(58) Field of Classification Search
CPC ...... B60W 30/18; B60W 10/06; B60W 10/10; B60W 10/18
USPC .......................................................... 701/45
See application file for complete search history.

(56) References Cited

U.S. PATENT DOCUMENTS

| | | | | |
|---|---|---|---|---|
| 9,751,534 B2 * | 9/2017 | Fung | ..................... | B60W 40/08 |
| 2010/0294583 A1 * | 11/2010 | Biondo | ................ | B60K 28/063 |
| | | | | 180/272 |
| 2016/0001781 A1 * | 1/2016 | Fung | ..................... | G06F 19/345 |
| | | | | 701/36 |

* cited by examiner

*Primary Examiner* — Yazan A Soofi

(57) ABSTRACT

A method and apparatus for detecting impairment of a vehicle operator are provided. The method includes detecting a first impairment level at a first time; detecting a second impairment level at a second time after the first time; based on the detected first impairment level and the detected second impairment level, determining a third impairment level at a third time after the second time; and inhibiting vehicle operation in response to determining that the third impairment level is greater than an impairment threshold. The apparatus and method may be used in a vehicle or other apparatus to prevent vehicle operator from operating the vehicle while impaired or prior to becoming impaired.

20 Claims, 4 Drawing Sheets

METHOD AND APPARATUS FOR DETECTING PROJECTED IMPAIRMENT

INTRODUCTION

Apparatuses and methods consistent with exemplary embodiments relate to impairment detection. More particularly, apparatuses and methods consistent with exemplary embodiments relate to impairment detection in vehicles.

SUMMARY

One or more exemplary embodiments provide a method and an apparatus that project a future impairment level of a vehicle operator. More particularly, one or more exemplary embodiments provide a method and an apparatus that project a future impairment level of a vehicle operator and inhibit the operation of the vehicle if the projected impairment level exceeds an acceptable level.

According to an aspect of an exemplary embodiment, a method for detecting impairment of a vehicle operator is provided. The method includes: detecting a first impairment level; in response to determining that the first impairment level is greater than a first impairment threshold, determining whether the first impairment level is greater than a second impairment threshold; in response to determining that the first impairment level is greater than the second impairment threshold, inhibiting a vehicle operation; in response to determining that the first impairment level is less than the second impairment threshold, detect a second impairment level; based on the first impairment level and the second impairment level, determine a third impairment level at a future time; and in response to determining that the third impairment level is greater than the second impairment threshold, inhibiting the vehicle operation.

The detecting the second impairment level may include: outputting a notification requesting a sample; determining whether the sample has been provided; and in response to determining that the sample has not been provided within a predetermined period of time, re-outputting the notification requesting the sample.

The detecting the first impairment level and the detecting the second impairment level may include detecting blood alcohol content of a vehicle operator.

The first impairment threshold may be less than the second impairment threshold.

The first impairment threshold may include a blood alcohol content threshold and the second impairment threshold may also include a blood alcohol content threshold.

The future time may be at least 45 minutes from a time that the first impairment level is detected.

The detecting a first impairment level may include: receiving a blood alcohol measurement; and detecting the first impairment level based on the received blood alcohol measurement.

The blood alcohol measurement may be received from at least one from among a breathalyzer, an infrared sensor, a near infrared tissue spectrometry sensor, a distance spectrometry sensor, an electrochemical sensor, and a laser sensor.

The inhibiting the vehicle operation may include at least one from among inhibiting movement of a vehicle, disabling an ignition of a vehicle maintaining a transmission of the vehicle in a stationary state, and engaging a brake.

According to an aspect of another exemplary embodiment, an apparatus for detecting impairment of a vehicle operator is provided. The apparatus includes: at least one memory comprising computer executable instructions; and at least one processor configured to read and execute the computer executable instructions. The computer executable instructions cause the at least one processor to: detect a first impairment level at a first time; detect a second impairment level at a second time after the first time; based on the detected first impairment level and the detected second impairment level, determine a third impairment level at a third time after the second time; and inhibit vehicle operation in response to determining that the third impairment level is greater than an impairment threshold.

The at least one processor may be further configured to detect the second impairment level by outputting a notification requesting a sample, determining whether the sample has been provided, and in response to determining that the sample has not been provided within a predetermined period of time, re-outputting the notification requesting the sample.

The at least one processor may be further configured to detect the first impairment level and the second impairment level based on a blood alcohol measurement received from at least one from among a breathalyzer, an infrared sensor, a near infrared tissue spectrometry sensor, a distance spectrometry sensor, an electrochemical sensor, and a laser sensor.

The first impairment level, the second impairment level, the third impairment level may include a blood alcohol level.

The at least one processor may be further configured to control to inhibit the vehicle operation by performing at least one from among inhibiting movement of a vehicle, disabling an ignition of a vehicle maintaining a transmission of the vehicle in a stationary state, and engaging a brake.

The third time may be at least 45 minutes from the third time

The impairment threshold may be set based on driver profile information, the driver profile information including information on at least one from among an age of a driver, a location of a driver, a weight of a driver, conviction information of a driver, and driving restrictions of a driver.

According to an aspect of another exemplary embodiment, a non-transitory computer readable medium comprising computer executable instructions executable by a processor to perform the method for detecting impairment of a vehicle operator. The method includes: receiving impairment information, the impairment information including a plurality of impairment levels measured at a plurality of times, respectively; based on the received impairment information, selecting an impairment projection model from among a plurality of impairment projection models; determining a projected impairment level based on the impairment information and the selected impairment projection model; and inhibiting vehicle operation in response to determining that the projected impairment level is greater than an impairment threshold.

The plurality of impairment projection models may include at least two from among a linear regression model, a linear projection model, a curve fitting model, a table lookup interpolation model, and a polynomial regression model.

The selecting the impairment projection model from among the plurality of impairment projection models may include selecting the impairment projection model that projects a greatest impairment level from among impairment levels calculated from the plurality of impairment projection models. The selecting the impairment projection model from among the plurality of impairment projection models may include selecting the impairment projection model that projects a most accurate impairment level from among impairment levels calculated from the plurality of impairment projection models.

Other objects, advantages and novel features of the exemplary embodiments will become more apparent from the following detailed description of exemplary embodiments and the accompanying drawings.

DETAILED DESCRIPTION

Figure 1:
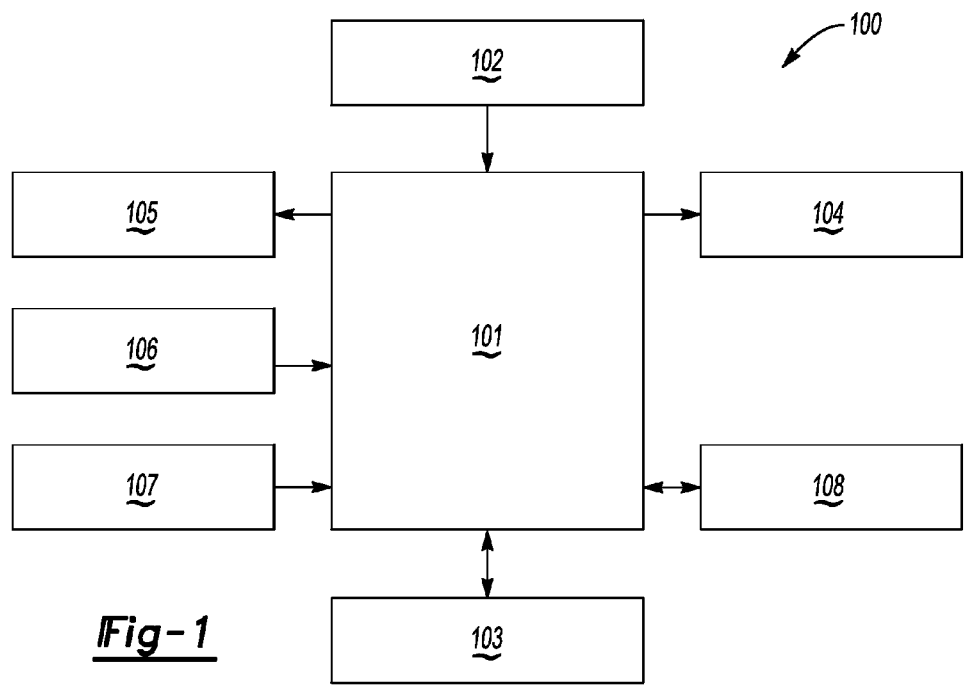
FIG. 1 shows a block diagram of an apparatus that detects impairment according to an exemplary embodiment.

An apparatus and method that detect impairment will now be described in detail with reference to FIGS. 1-5 of the accompanying drawings in which like reference numerals refer to like elements throughout.

The following disclosure will enable one skilled in the art to practice the inventive concept. However, the exemplary embodiments disclosed herein are merely exemplary and do not limit the inventive concept to exemplary embodiments described herein. Moreover, descriptions of features or aspects of each exemplary embodiment should typically be considered as available for aspects of other exemplary embodiments.

It is also understood that where it is stated herein that a first element is "connected to," "formed on," or "disposed on" a second element, the first element may be connected directly to, formed directly on or disposed directly on the second element or there may be intervening elements between the first element and the second element, unless it is stated that a first element is "directly" connected to, formed on, or disposed on the second element. In addition, if a first element is configured to "receive" or "send" information from or to a second element, the first element may "receive" or "send" the information directly from or directly to the second element, receive or send the information via a bus, receive or send the information via a network, or receive or send the information via intermediate elements, unless the first element is indicated to receive information "directly" from the second element.

Throughout the disclosure, one or more of the elements disclosed may be combined into a single device or combined into one or more devices. In addition, individual elements may be provided on separate devices.

An impaired individual may lose the ability to effectively operate a vehicle and/or other equipment. Impairment refers to a diminished cognitive and/or physical ability caused by substances such as alcohol or drugs. Thus, it is beneficial to detect whether an individual is impaired and to prevent the individual from operating a vehicle and/or other equipment.

Impairment detection may be implemented in many forms. For example, an impairment sensor such as a breathalyzer, an infrared sensor, a camera an eye scanner, etc., may detect whether an individual is impaired. Moreover, fluids such as urine, saliva, blood, as well as hair, skin and breath samples may be tested to detect the presence of substances that indicate that a subject is impaired. However, impairment detection usually detects a present state of impairment and does not account for absorption of substances that have already been ingested by an individual and that will increase the impairment of an individual as they are absorbed by the individual's body over time.

FIG. 1 shows a block diagram of an apparatus for determining projected impairment 100 (i.e., an apparatus for detecting impairment) according to an exemplary embodiment. As shown in FIG. 1, the apparatus for detecting impairment 100, according to an exemplary embodiment, includes a controller 101, a power supply 102, a storage 103, an output 104, a vehicle operation inhibitor 105, a user input 106, an impairment sensor 107, and a communication device 108. However, the apparatus for detecting impairment 100 is not limited to the aforementioned configuration and may be configured to include additional elements and/or omit one or more of the aforementioned elements.

The controller 101 controls the overall operation and function of the apparatus for detecting impairment 100. The controller 101 may control one or more of a storage 103, an output 104, a vehicle operation inhibitor 105, a user input 106, an impairment sensor 107, and a communication device 108 of the apparatus for detecting impairment 100. The controller 101 may include one or more from among a processor, a microprocessor, a central processing unit (CPU), a graphics processor, Application Specific Integrated Circuits (ASICs), Field-Programmable Gate Arrays (FPGAs), state machines, and a combination of hardware, software and firmware components.

The controller 101 is configured to send and/or receive information from one or more of the storage 103, the output 104, the vehicle operation inhibitor 105, the user input 106, the impairment sensor 107, and the communication device 108 of the apparatus for detecting impairment 100. The information may be sent and received via a bus or network, or may be directly read or written to/from one or more of the storage 103, the output 104, the vehicle operation inhibitor 105, the user input 106, the impairment sensor 107, and the communication device 108 of the apparatus for detecting impairment 100.

The power supply 102 provides power to one or more of the controller 101, the storage 103, the output 104, the vehicle operation inhibitor 105, the user input 106, the impairment sensor 107, and the communication device 108 of the apparatus for detecting impairment 100. The power supply 102 may include one or more from among a battery, an outlet, a capacitor, a solar energy cell, a generator, a wind energy device, an alternator, etc.

The storage 103 is configured for storing information and retrieving information used by the apparatus for detecting impairment 100. The storage 103 may be controlled by the controller 101 to store and retrieve impairment information such as an impairment level, etc. The storage 103 may also include the computer instructions configured to be executed by a processor to perform the functions of the apparatus for detecting impairment 100.

The storage 103 may include one or more from among floppy diskettes, optical disks, CD-ROMs (Compact Disc- Read Only Memories), magneto-optical disks, ROMs (Read Only Memories), RAMs (Random Access Memories), EPROMs (Erasable Programmable Read Only Memories), EEPROMs (Electrically Erasable Programmable Read Only Memories), magnetic or optical cards, flash memory, cache memory, and other type of media/machine-readable medium suitable for storing machine-executable instructions.

The impairment information may include one or more from among blood alcohol content, an amount or concentration of predetermined drug, an amount or concentration of impairing or intoxicating substance. The predetermined drug or intoxicating substance may include prescription drugs as well as illegal drugs or substances. For example, measurements of one or more from among alcohol, opiates, cocaine, THC, marijuana, and methamphetamines, etc., and/or chemical compositions and bi-products associated with the aforementioned substances may be included in the impairment information.

The output 104 outputs information in one or more forms including: visual, audible and/or haptic form. The output 104 may be controlled by the controller 101 to provide outputs to the user of the apparatus for detecting impairment 100. The output 104 may include one or more from among a speaker, a centrally-located a display, a head up display, a windshield display, a haptic feedback device, a vibration device, a tactile feedback device, a tap-feedback device, a holographic display, an instrument light, an instrument display, an indicator light, etc.

The output 104 may output notification including one or more from among an audible notification, a light notification, and a display notification. The notification may include information regarding an impairment level or information indicating that vehicle operations have been inhibited or disabled.

The vehicle operation inhibitor 105 is configured to inhibit or disable one or more operations of the vehicle. For example, the vehicle operation inhibitor 105 may disable one or more from among a transmission from shifting, ignition from starting a vehicle, ignition from starting an engine of a vehicle, forward movement of a vehicle, a steering wheel from moving, etc.

The user input 106 is configured to provide information and commands to the apparatus for detecting impairment 100. The user input 106 may be used to provide user inputs, etc. to the controller 101. The user input 106 may include one or more from among a touchscreen, a keyboard, a soft keypad, a button, a motion detector, a voice input detector, a microphone, a camera, a trackpad, a mouse, a touchpad, etc. The user input 106 may be configured to receive a user input to acknowledge or dismiss the notification output by the output 104. The user input 106 may also be configured to receive a user input to cycle through notifications or different screens of a notification.

The impairment sensor 107 is configured to detect an impairment level of an individual such as an operator of the vehicle and provide impairment information to the controller 101. The impairment sensor 107 may include one or more from among a breathalyzer, an infrared sensor, a near infrared tissue spectrometry sensor, a distance spectrometry sensor, an electrochemical sensor, an eye scanner, a laser sensor, a camera, a microphone, a motion detector, a driving performance sensor, an ocular movement sensor, and a behavioral sensor, etc. The impairment information may be received directly from the impairment sensor 107, may be read from storage 103, or received via communication device 108.

The motion performance sensor may detect that the driving performance is below an acceptable threshold based on parameters including one or more from among posted speed, vehicle speed, reaction time, lane departures by a vehicle, and vehicle trajectory. The behavioral sensor may detect impaired behavior based on one or more from among a vehicle operators movements, a gaze of a vehicle operator, a speech of a vehicle operator, etc.

Moreover, in an exemplary embodiment, the impairment sensor 107 may be configured to scan fluids, such as one or more from among urine, saliva, and/or blood, and/or scan hair, skin and breath to detect the presence, amount, and/or concentration of substances that indicate that a subject is impaired. The substance may include alcohol, a predetermined drug such as a prescription drug or illegal drug. For example, the impairment sensor 107 may scan for one or more from among alcohol, opiates, cocaine, THC, marijuana, and methamphetamines, etc., and/or chemical compositions and bi-products associated with the aforementioned substances.

According to another example, a laser sensor may transmit a laser to ping the dermis and excite molecules of the impairing substance. The laser may then be used to measure the amount of the impairing substance present in capillary blood. The impairment sensor 107 may provide information on the aforementioned substances to be included in the impairment information. For example, the impairment information may include one or more from among blood alcohol content, amount or concentration of predetermined drug, amount or concentration of impairing or intoxicating substance, and an impaired status of a vehicle operator.

The communication device 108 may be used by apparatus for detecting impairment 100 to communicate with various types of external apparatuses according to various communication methods. The communication device 108 may be used to send impairment information to the controller 101 of the apparatus for detecting impairment 100. The communication device 108 may also be configured to transmit the notification of impairment to a mobile device such as mobile phone, smart watch, laptop, tablet, etc. so that the notification is output by the mobile device. Moreover, the communication device 108 may transmit the notification of impairment to a law enforcement agency, transportation service, family member, or other designated contact along with location information indicating a location of a vehicle or impaired individual. The location information may be determined from information received from a global positioning system (GPS) receiver.

The communication device 108 may include various communication modules such as one or more from among a broadcast receiving module, a near field communication (NFC) module, a GPS receiver, a wired communication module, or a wireless communication module. The broadcast receiving module may include a terrestrial broadcast receiving module including an antenna to receive a terrestrial broadcast signal, a demodulator, and an equalizer, etc. The NFC module is a module that communicates with an external apparatus located at a nearby distance according to an NFC method. The GPS receiver is a module that receives a GPS signal from a GPS satellite and detects a current location. The wired communication module may be a module that receives information over a wired network such as a local area network, a controller area network (CAN), or an external network. The wireless communication module is a module that is connected to an external network by using a wireless communication protocol such as Wi-Fi or IEEE communication protocol and communicates with the external network. The wireless communication module may further include a mobile communication module that accesses a mobile communication network and performs communication according to various mobile communication standards such as 3$^{rd}$ generation (3G), 3$^{rd}$ generation partnership project (3GPP), long term evolution (LTE), Bluetooth, or ZigBee.

According to an exemplary embodiment, the controller 101 of the apparatus for detecting impairment 100 is configured to detect a first impairment level. In response to determining that the first impairment level is greater than a first impairment threshold, the controller 101 may be configured to determine whether the first impairment level is greater than a second impairment threshold. In response to determining that the first impairment level is greater than the second impairment threshold, the controller 101 may be configured to inhibit a vehicle operation. In response to determining that the first impairment level is less than the second impairment threshold, the controller 101 may be configured to detect a second impairment level. Then, based on the first impairment level and the second impairment level, the controller 101 may be configured to determine a projected third impairment level at a future time; and in response to determining that the third impairment level is greater than the second impairment threshold, the controller 101 may be configured inhibit the vehicle operation. The first impairment threshold may be less than the second impairment threshold. The first impairment threshold may also be a blood alcohol content threshold and the second impairment threshold may be a blood alcohol content threshold. The future time may be at least 45 minutes from a time that the first impairment level is detected.

An impairment threshold may be set according to is set based on driver profile information. The driver profile information may include information on at least one from among an age of a driver, a location of a driver, a weight of a driver, conviction information of a driver, and driving restrictions of a driver.

According to another exemplary embodiment, the controller 101 of the apparatus for detecting impairment 100 may be configured to detect a first impairment level at a first time, detect a second impairment level at a second time after the first time. Then, based on the detected first impairment level and the detected second impairment level, the controller 101 may determine a third impairment level at a third time after the second time. The controller 101 would then inhibit vehicle operation in response to determining that the third impairment level is greater than an impairment threshold.

The controller 101 may control the output 104 to output a notification requesting a sample. The controller 101 may then determine whether the sample has been provided to impairment sensor 107. In response to determining that the sample has not been provided within a predetermined period of time, the controller 101 my control output 104 to re-output the notification requesting the sample.

The controller 101 may control the vehicle operation inhibitor 105 to inhibit the vehicle operation by temporarily disabling or inhibiting the operation of one or more from among transmission shifter, an ignition switch, a power switch or button, a steering wheel, etc.

Figure 2:
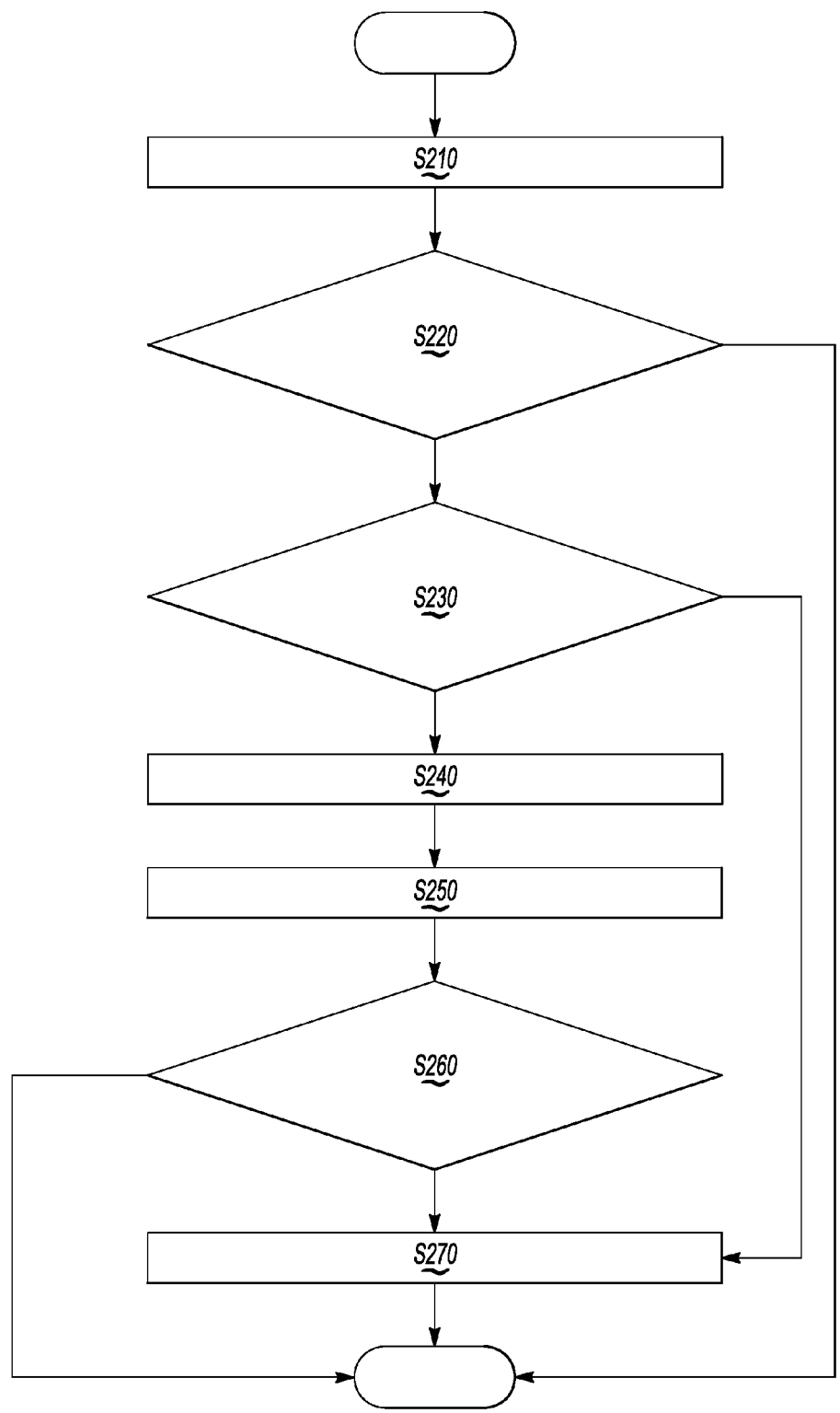
FIG. 2 shows a flowchart for a method of detecting impairment according to an aspect of an exemplary embodiment.

FIG. 2 shows a flowchart for a method for detecting impairment of a vehicle operator according to an exemplary embodiment. The method of FIG. 2 may be performed by the apparatus for detecting impairment 100 or may be encoded into a computer readable medium as instructions that are executable by a computer to perform the method.

Referring to FIG. 2, a first impairment level is detected in operation S210. Then it is determined whether the first impairment level is greater than a first impairment threshold in operation S220. If the first impairment level is less than the first impairment threshold (operation S220-NO), the process ends. If the first impairment level is greater than or equal to the first impairment threshold (operation S220-YES), it is determined whether the first impairment level is greater than a second impairment threshold (operation S230). If the first impairment level is greater than or equal to the second impairment threshold (operation S230-YES), the vehicle operation is inhibited in operation S270. If the first impairment level is less than the second impairment threshold (operation S230-NO), a second impairment level is detected in operation S240.

Next, in operation S250, a projected third impairment level for a future time is determined. In one example, the projected third impairment level is determined based on the detected first impairment level and the detected second impairment level. According to another example, the projected third impairment level may be determined by a linear regression analysis, table lookup interpolation, polynomial regression, curve fit regression, etc. In operation S260, it is determined whether the third impairment level is greater than the second impairment threshold. If the third impairment level is greater than or equal the second impairment threshold (operation S260-YES), the vehicle operation is inhibited in operation S270. If the third impairment level is less than the second impairment threshold (operation S260-NO), the process ends.

Figure 3:
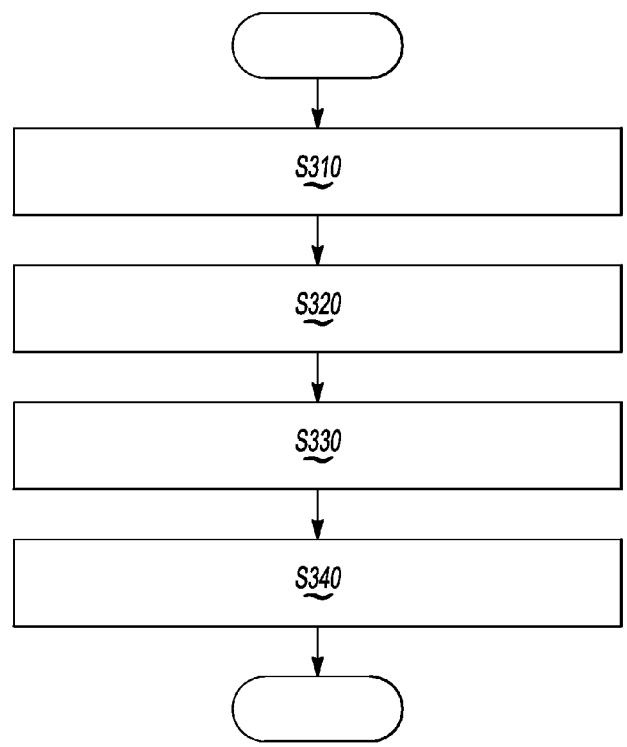
FIG. 3 shows a flowchart for a method of detecting impairment according to an aspect of another exemplary embodiment.

FIG. 3 shows a flowchart for a method for detecting impairment of a vehicle operator according to another exemplary embodiment. The method of FIG. 3 may be performed by the apparatus for detecting impairment 100 or may be encoded into a computer readable medium as instructions that are executable by a computer to perform the method.

Referring to FIG. 3, a first impairment level is detected at a first point in time in operation S310. Next a second impairment level is detected at a second point in time in operation S320. Based on the detected first impairment level and the detected second impairment level, a third impairment level is projected for a third time in the future in operation S330. In response the third impairment level being greater than a predetermined impairment threshold, the operation of the vehicle is inhibited in operation S340.

The projected third impairment level may be calculated by determining increase information, which is the increase between the first impairment level and the second impairment level over the time that elapsed between a first time that the first impairment level is measured and a second time that the second impairment level is measured. In other words, the increase information may be calculated by taking a slope between the first impairment level and the second impairment level. This increase information is then multiplied by the amount of time between the second time that the second impairment level is measured and a third time (future time) at which the projected third impairment level is to be determined. The product of the increase information and the difference between the second time and the third time is then added to measured second impairment level to arrive at the projected third impairment level.

Figure 4A:
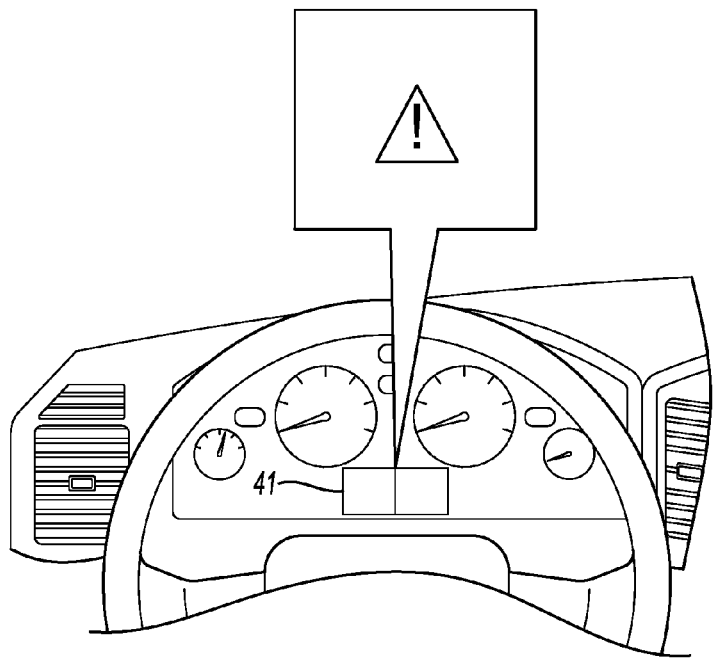
FIG. 4A shows an example of a first type of notification to warn of impairment according to an aspect of another exemplary embodiment.

FIG. 4A shows an example of a first type of notification to provide a notification of driver impairment according to an aspect of another exemplary embodiment. Referring to FIG. 4A, a first type of notification 41 to provide a notification of driver impairment is provided in a notification panel in the instrument cluster. The notification 41 may contain one or more from among text and/or an image indicating impairment, a notification that the vehicle is disabled, and a selectable element to request a transportation service or contact a pre-selected contact.

Figure 4B:
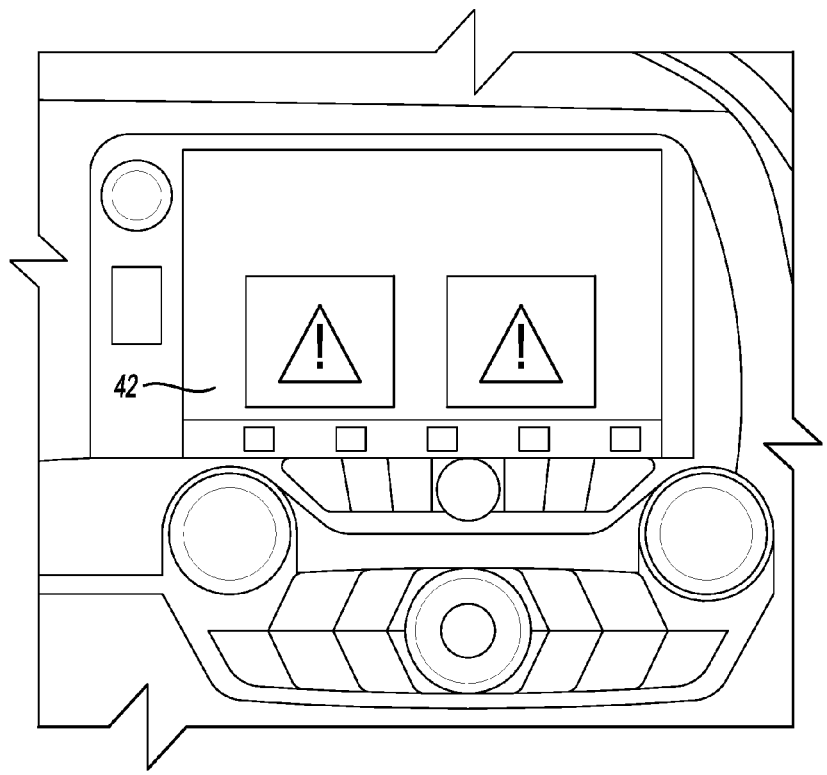
FIG. 4B shows an example of a second type notification to warn of impairment according to an aspect of another exemplary embodiment.

FIG. 4B shows an example of a second type of notification to provide a notification of driver impairment according to an aspect of another exemplary embodiment. Referring to FIG. 4B, a second type of notification 42 to provide a notification of driver impairment is provided in a center console display in vehicle. The notification 42 may contain one or more from among text and/or an image indicating impairment, a notification that the vehicle is disabled, and a selectable element to request a transportation service or contact a pre-selected contact.

Figure 5:
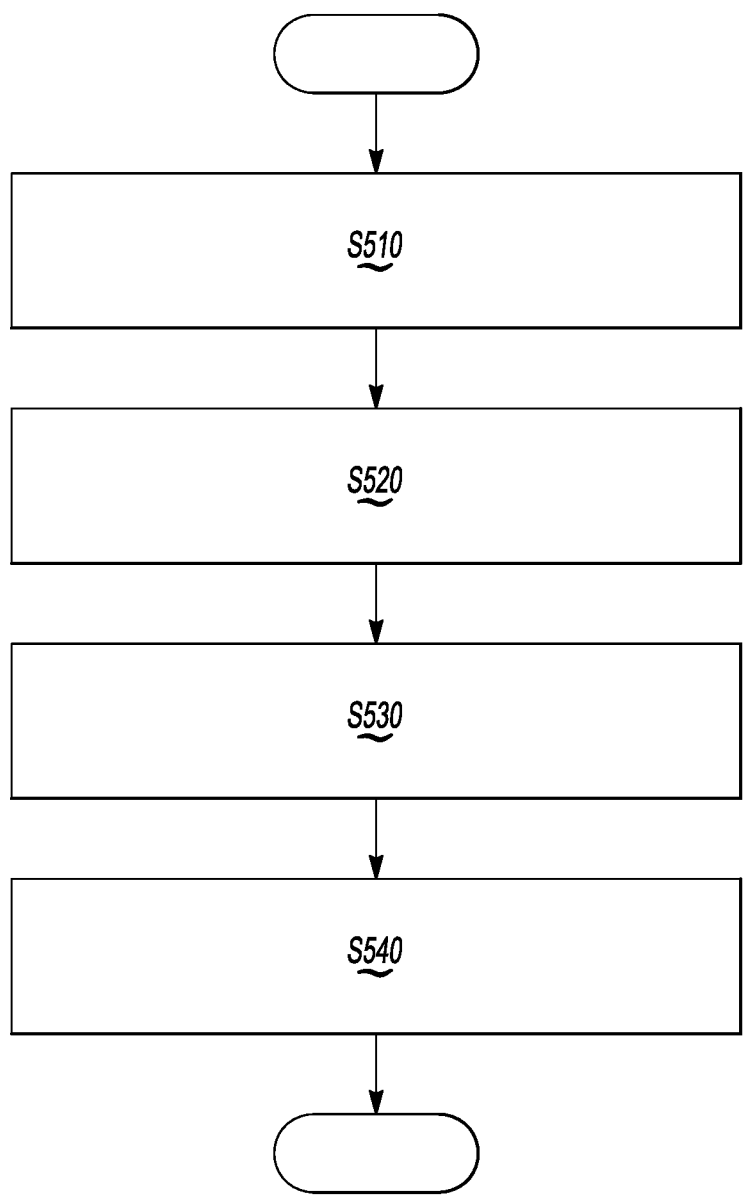
FIG. 5 shows a flowchart for a method for detecting impairment of a vehicle operator according to an aspect of another exemplary embodiment.

FIG. 5 shows a flowchart for a method for detecting impairment of a vehicle operator according to an aspect of another exemplary embodiment. The method of FIG. 5 may be performed by the apparatus for detecting impairment 100 or may be encoded into a computer readable medium as instructions that are executable by a computer to perform the method.

Referring to FIG. 5, impairment information including a plurality of impairment levels measured at a plurality of times, respectively, is received in operation S510. In operation S520, based on the received impairment information, an impairment projection model from among a plurality of impairment projection models is selected.

The selected impairment projection model may be the most accurate or appropriate impairment projection model for a given set of impairment information. Alternatively, the selected impairment projection model may be the impairment projection model that projects a greatest impairment level from among impairment levels calculated from the plurality of impairment projection models. The impairment projection models may include one or more from among a linear regression model, a linear projection model, a curve fitting model, a table lookup interpolation model, and a polynomial regression model.

A projected impairment level based on the impairment information and the selected impairment projection model is then determined in operation S530. In response to determining that the projected impairment level is greater than an impairment threshold, the operation of the vehicle is inhibited in operation S540.

The processes, methods, or algorithms disclosed herein can be deliverable to/implemented by a processing device, controller, or computer, which can include any existing programmable electronic control device or dedicated electronic control device. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

One or more exemplary embodiments have been described above with reference to the drawings. The exemplary embodiments described above should be considered in a descriptive sense only and not for purposes of limitation. Moreover, the exemplary embodiments may be modified without departing from the spirit and scope of the inventive concept, which is defined by the following claims.

What is claimed is:

1. A method for detecting impairment of a vehicle operator, the method comprising:
    detecting a first impairment level;
    in response to determining that the first impairment level is greater than a first impairment threshold, determining whether the first impairment level is greater than a second impairment threshold;
    in response to determining that the first impairment level is greater than the second impairment threshold, inhibiting a vehicle operation;
    in response to determining that the first impairment level is less than the second impairment threshold, detect a second impairment level;
    based on the first impairment level and the second impairment level, determine a third impairment level at a future time; and
    in response to determining that the third impairment level is greater than the second impairment threshold, inhibiting the vehicle operation,
    wherein the first, second, and third impairment levels are levels corresponding to a presence of a substance in a subject that indicates the subject has a diminished cognitive or physical ability caused by the substances, and
    wherein the first impairment threshold and the second impairment threshold are preset thresholds corresponding to detectable substances that cause the diminished cognitive or physical ability.

2. The method of claim 1, wherein the detecting the second impairment level comprises:
    outputting a notification requesting a sample;
    determining whether the sample has been provided; and
    in response to determining that the sample has not been provided within a predetermined period of time, re-outputting the notification requesting the sample.

3. The method of claim 1, wherein the detecting the first impairment level and the detecting the second impairment level comprise detecting blood alcohol content of a vehicle operator.

4. The method of claim 1, wherein the first impairment threshold is less than the second impairment threshold.

5. The method of claim 1, wherein the first impairment threshold comprises a blood alcohol content threshold and the second impairment threshold comprises a blood alcohol content threshold.

6. The method of claim 1, wherein the future time comprises at least 45 minutes from a time that the first impairment level is detected.

7. The method of claim 1, wherein the detecting a first impairment level comprises:
    receiving a blood alcohol measurement; and
    detecting the first impairment level based on the received blood alcohol measurement.

8. The method of claim 7, wherein the blood alcohol measurement is received from at least one from among a breathalyzer, an infrared sensor, a near infrared tissue spectrometry sensor, a distance spectrometry sensor, an electrochemical sensor, and a laser sensor.

9. The method of claim 1, wherein the inhibiting the vehicle operation comprises at least one from among inhibiting movement of a vehicle, disabling an ignition of a vehicle maintaining a transmission of the vehicle in a stationary state, and engaging a brake.

10. A non-transitory computer readable medium comprising computer executable instructions executable by a processor to perform the method of claim 1.

11. An apparatus for detecting impairment of a vehicle operator, the apparatus comprising:
   at least one memory comprising computer executable instructions; and
   at least one processor configured to read and execute the computer executable instructions, the computer executable instructions causing the at least one processor to:
   detect a first impairment level at a first time;
   detect a second impairment level at a second time after the first time;
   based on the detected first impairment level and the detected second impairment level, determine a third impairment level at a third time after the second time; and
   inhibit vehicle operation in response to determining that the third impairment level is greater than an impairment threshold,
   wherein the first, second, and third impairment levels are levels corresponding to a presence of a substance in a subject that indicates the subject has a diminished cognitive or physical ability caused by the substances, and
   wherein the first impairment threshold and the second impairment threshold are preset thresholds corresponding to detectable substances that cause the diminished cognitive or physical ability.

12. The apparatus of claim 11, wherein the at least one processor is further configured to detect the second impairment level by outputting a notification requesting a sample, determining whether the sample has been provided, and in response to determining that the sample has not been provided within a predetermined period of time, re-outputting the notification requesting the sample.

13. The apparatus of claim 11, wherein the at least one processor is further configured to detect the first impairment level and the second impairment level based on a blood alcohol measurement received from at least one from among a breathalyzer, an infrared sensor, a near infrared tissue spectrometry sensor, a distance spectrometry sensor, an electrochemical sensor, and a laser sensor.

14. The apparatus of claim 11, wherein the first impairment level, the second impairment level, the third impairment level comprise a blood alcohol level.

15. The apparatus of claim 11, wherein the at least one processor is further configured to control to inhibit the vehicle operation by performing at least one from among inhibiting movement of a vehicle, disabling an ignition of a vehicle maintaining a transmission of the vehicle in a stationary state, and engaging a brake.

16. The apparatus of claim 11, wherein the third time is at least 45 minutes from the third time.

17. The apparatus of claim 11, wherein the impairment threshold is set based on driver profile information, the driver profile information comprising information on at least one from among an age of a driver, a location of a driver, a weight of a driver, conviction information of a driver, and driving restrictions of a driver.

18. A non-transitory computer readable medium comprising computer executable instructions executable by a processor to perform a method for detecting impairment of a vehicle operator, the method comprising:
   receiving impairment information, the impairment information including a plurality of impairment levels measured at a plurality of times, respectively;
   based on the received impairment information, selecting an impairment projection model from among a plurality of impairment projection models;
   determining a projected impairment level based on the impairment information and the selected impairment projection model; and
   inhibiting vehicle operation in response to determining that the projected impairment level is greater than an impairment threshold,
   wherein the plurality of impairment levels are levels corresponding to a presence of substance in a subject that indicates the subject has a diminished cognitive or physical ability caused by the substances, and
   wherein the impairment threshold corresponds to a detectable substance that cause the diminished cognitive or physical ability.

19. The non-transitory computer readable medium of claim 18, wherein the plurality of impairment projection models comprise at least two from among a linear regression model, a linear projection model, a curve fitting model, a table lookup interpolation model, and a polynomial regression model.

20. The non-transitory computer readable medium of claim 18, wherein the selecting the impairment projection model from among the plurality of impairment projection models comprises selecting the impairment projection model that projects a greatest impairment level from among impairment levels calculated from the plurality of impairment projection models.

* * * * *